(12) United States Patent
Hyder

(10) Patent No.: US 11,471,300 B2
(45) Date of Patent: *Oct. 18, 2022

(54) SYSTEM, DEVICE, AND METHOD FOR TRANSFORAMINAL LUMBAR INTERBODY FUSION

(71) Applicant: LIFE SPINE, INC., Huntley, IL (US)

(72) Inventor: Zeshan Hyder, Munster, IN (US)

(73) Assignee: Life Spine, Inc., Huntley, IL (US)

( * ) Notice: Subject to any disclaimer, the term of this patent is extended or adjusted under 35 U.S.C. 154(b) by 287 days.

This patent is subject to a terminal disclaimer.

(21) Appl. No.: 16/669,035

(22) Filed: Oct. 30, 2019

(65) Prior Publication Data
US 2020/0060842 A1  Feb. 27, 2020

Related U.S. Application Data

(63) Continuation of application No. 15/473,118, filed on Mar. 29, 2017, now Pat. No. 10,463,503.

(60) Provisional application No. 62/314,626, filed on Mar. 29, 2016.

(51) Int. Cl.
| | |
|---|---|
| *A61F 2/46* | (2006.01) |
| *A61F 2/44* | (2006.01) |
| *A61F 2/30* | (2006.01) |

(52) U.S. Cl.
CPC ............ *A61F 2/447* (2013.01); *A61F 2/4611* (2013.01); *A61F 2002/3082* (2013.01); *A61F 2002/30112* (2013.01); *A61F 2002/30556* (2013.01); *A61F 2002/30579* (2013.01); *A61F 2002/30593* (2013.01); *A61F 2002/30617* (2013.01); *A61F 2002/30772* (2013.01); *A61F 2002/4629* (2013.01)

(58) Field of Classification Search
CPC ............................... A61F 2/4611; A61F 2/447
See application file for complete search history.

(56) References Cited

U.S. PATENT DOCUMENTS

| | | | | |
|---|---|---|---|---|
| 2013/0245767 | A1* | 9/2013 | Lee | ........................ A61F 2/447 623/17.16 |
| 2014/0088711 | A1* | 3/2014 | Chin | ................... A61F 2/30749 623/17.16 |

* cited by examiner

*Primary Examiner* — Si Ming Ku
(74) *Attorney, Agent, or Firm* — Foley & Lardner LLP

(57) ABSTRACT

A kit for installing a spine implant includes an installation tool and a spine implant. The spine implant includes a body having a cavity extending through the body, a channel extending a first length along the first lateral side, a bore in communication with the cavity, a superior blade guide, and an inferior blade guide. The body also includes a first blade situated on the superior blade guide and movable along the superior blade guide after implantation of the, and a second blade situated on the inferior blade movable along the inferior blade guide after implantation of the body. The installation tool includes a handle, a hollow shaft connected to the handle, a pusher rod configured to extend through the hollow shaft and extend the first and second blades, and a graft rod configured to extend through the hollow shaft and introduce graft material into the spine implant.

8 Claims, 3 Drawing Sheets

SYSTEM, DEVICE, AND METHOD FOR TRANSFORAMINAL LUMBAR INTERBODY FUSION

CROSS REFERENCE TO RELATED APPLICATIONS

This application is a continuation of U.S. application Ser. No. 15/473,118, filed Mar. 29, 2017, which is hereby incorporated herein by reference in its entirety, which claims the benefit of and priority to provisional U.S. patent application Ser. No. 62/314,626, filed Mar. 29, 2016, which is hereby incorporated herein by reference in its entirety.

TECHNICAL FIELD

The present invention relates to methods and devices for orthopedic surgery of the spine and, particularly, to methods and devices for transforaminal lumbar interbody fusion (TLIF).

BACKGROUND

Many people contend with spine issues as a result of age, disease, and trauma, as well as congenital and acquired complications and conditions. While some of these issues can be alleviated without surgery, other issues necessitate surgery. Spinal fusion may be recommended for conditions such as spondylolistheses, degenerative disc disease, or recurrent disc herniation, and is designed to create solid bone between adjacent vertebrae, thereby eliminating any movement between the bones. A spinal fusion uses an implant or device known as an interbody cage or spacer along with bone graft and/or bone graft substitute that is inserted into the disc space between adjacent vertebrae from one side of the spine. Typically, additional surgical hardware (implants) such as pedicle screws and rods or plates are attached to the back of the vertebrae. As the bone graft heals, it fuses the adjacent vertebrae to form one long vertebra.

A fusion of the lumbar region of the spine (a lumbar fusion) may be accomplished using several techniques. Once such technique is known as a transforaminal lumbar interbody fusion or TLIF. TLIF spine surgery is performed through the posterior aspect of the spine and provides stabilization of the anterior portion by an interbody cage and bone graft while the posterior portion is locked in place with pedicle screws, rods and bone graft. A TLIF procedure is advantageous over a posterior lumbar interbody fusion (PLIF) and other lumbar fusion procedures for several reasons. In a TLIF procedure, bone fusion is enhanced because bone graft is not only placed along the "gutters" of the spine posteriorly, but also in the disc space. A TLIF procedure also allows the surgeon to insert bone graft and an interbody cage into the disc space laterally from a unilateral approach without forcefully retracting the nerve roots as much as the PLIF approach, which can reduce injury and scarring around the nerve roots. However, there is room for improvement over current TLIF implants, instruments, and/or surgical procedures.

In view of the above, it is an object of the present invention to provide an improved TLIF implant, an instrument for implanting the improved TLIF, and/or a surgical procedure for the implantation.

SUMMARY

An implant, instrument, and procedure for a transforaminal lumbar interbody fusion (TLIF) is provided.

The TLIF implant is characterized by a body having a cavity, an unthreaded hole in an end of the body that is in communication with the cavity, a first slot extending along an outside surface of a first lateral wall of the body, and a second slot extending along an outside surface of a second lateral wall of the body, the first and second slots configured to receive an installation tool for holding the TLIF implant. The cavity houses a first impacted blade and a second impacted blade. When driven by the installation tool, guides formed in the walls of the cavity direct the first and second impacted blades along the inside of the cavity such that ends of the first and second blades extend from the cavity and beyond the implant body.

The end of the first impacted blade extends from an upper side of the cavity and beyond the implant body, while the end of the second impacted blade extends from a lower side of the cavity and beyond the implant body.

The end of the first blade may be barbed. The end of the second blade may likewise be barbed.

Upper (superior) surfaces of the body of the TLIF implant and lower (inferior) surfaces of the body of the TLIF implant may each have serrations, teeth or otherwise.

The TLIF instrument is characterized by hollow shaft extending from a handle, the hollow shaft having a distal end with a first prong and a second prong, the first prong configured for releasable reception in the first slot of the TLIF implant body, and the second prong configured for releasable reception in the second slot of the TLIF implant body. The hollow shaft receives a movable rod that extends through the handle and hollow shaft, and has a length sufficient for a tip of the rod to extend into the cavity of the TLIF implant body when the TLIF implant body is held by the installation tool. The movable rod tip is configured to engage and push the first and second impacted blades of the TLIF implant such that ends of the first and second blades extend from the TLIF implant body.

A yoke may be disposed between the handle and the hollow shaft.

One or more windows (openings) may be formed in the hollow shaft in order to receive graft for insertion into the TLIF implant. One or more of the plurality of windows may have an oval shape.

The procedure or method of use/installation includes placing the present TLIF implant onto the present TLIF implant installation tool. The first and second prongs at the tip of the shaft of the installation tool are received in the first and second outside lateral slots of the TLIF implant body. The installation tool is thus ready to place the TLIF implant into the vertebral space previously occupied by a vertebra, the vertebra having been surgically removed prior to implant installation. Once the TLIF implant has been placed at the desired location, the moveable rod with configured tip is inserted into the hollow shaft of the installation tool and used to push the impacted blades up and out of the implant cavity. The movable blade pushing rod is removed from the hollow shaft of the installation tool and a graft pushing rod is received in the installation tool. Graft is inserted through the windows of the hollow tool shaft. The graft pushing rod is moved to push the graft through the hollow tool shaft and into the cavity of the installed TLIF implant through the end hole. Once a sufficient amount of graft has been pushed into the implant cavity, the rod and installation tool are removed.

Further aspects of the present invention will become apparent from consideration of the drawings and the following description of a form of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE FIGURES

The features of the invention will be better understood by reference to the accompanying drawings which illustrate the present invention, wherein.

DETAILED DESCRIPTION

Figure 1:
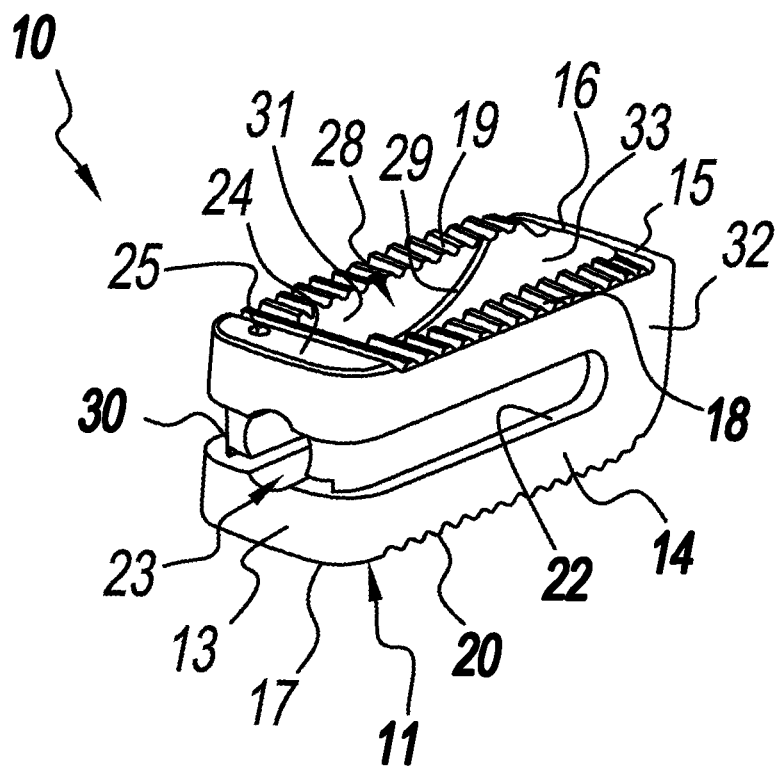
FIG. 1 is an isometric rear side view of an exemplary TLIF implant fashioned in accordance with the present principles.

Referring to FIG. 1, there is depicted an exemplary form of a transforaminal lumbar interbody fusion (TLIF) implant, generally designated 10, fashioned in accordance with the present principles. The TLIF implant 10 is made from a biocompatible material such as, but not limited to, titanium, stainless steel, an alloy of titanium or stainless steel, or otherwise. The TLIF implant 10 is characterized by a body 11 fashioned generally as a rectangular cuboid or prism having an upper (superior) surface 16, a lower (inferior) surface 17 opposite to the upper surface 16, a first lateral side 14, a second lateral side (not seen) that is opposite to and identical with the first lateral side 14, a first end 12, and a second end 13 opposite to the first end 12, the nomenclature "first" and "second" being arbitrary. The body 11 also has a cavity 28 that extends from the upper surface 16 to the lower surface 17. The cavity 28 is adapted or configured to received bone graft/bone graft material such as is known in the art.

The first end 12 of the body 11 defines a nose or arch having a downwardly angled or sloped upper (superior) surface 15, an upwardly angled or sloped lower (inferior) surface (not seen) opposite to the downwardly angled upper surface 15, a first slanted side 32, and a second slanted side (not seen) opposite to the first slanted side 32, the nomenclature "first" and "second" being arbitrary. A bore 26 (see FIG. 2) is provided in the downwardly angled upper surface 15 the purpose of which is to accept a radio opaque marker to mark the first end 12 of the implant. The second end 13 of the body 11 is generally planar with a large unthreaded bore 23 that extends/provides communication from the second end 13 into/to the cavity 28. A first elongated slot 22 runs from a first side of the bore 23 to and along the first lateral side 14, while a second elongated slot 30 runs from a second side of the bore 23 to and along the second lateral side, the nomenclature "first" and "second" being arbitrary. The first elongated slot 22 is adapted/configured to receive a first prong 107 of the installation tool 100 (see FIG. 2), while the second elongated slot 30 is adapted/configured to receive a second prong (not seen) of the installation tool 100 (see FIG. 2) opposite the first prong 107 as explained below, the nomenclature "first" and "second" being arbitrary. The first and second elongated slots preferably, but not necessarily, extend a majority of the length of the respective first and second lateral sides 14, (not seen). An upper (superior) surface 24 and a lower (inferior) surface (not seen) opposite the upper surface 24 of the second end 13 are generally planar. A bore 25 (see also FIG. 2) is provided in the upper surface 24 the purpose of which is to accept a radio opaque marker to mark the second end 13 of the implant.

Extending between the upper surface 24 of the second end 13 and the downwardly angled upper surface 15 adjacent the first lateral side 14 is a first section of serrations, teeth, or the like (collectively, serrations) 18, while extending between the upper surface 24 of the second end 13 and the downwardly angled upper surface 15 adjacent the second lateral side (not seen) is a second section of serrations, teeth, or the like (collectively, serrations) 19, the nomenclature "first" and "second" being arbitrary. The serrations 18, 19 provide gripping of the inferior end of a superior vertebra when implanted. In like manner, extending between the lower surface (not seen) of the second end 13 and the upwardly angled lower surface 27 adjacent the first lateral side 22 is a third section of serrations, teeth, or the like (collectively, serrations) 20, while extending between the lower surface (not seen) of the second end 13 and the upwardly angled lower surface 27 adjacent the second lateral side (not seen) is a fourth section of serrations, teeth, or the like (collectively, serrations) (not seen), the nomenclature "third" and "fourth" being arbitrary. The serrations 20, (not seen) provide gripping of the superior end of an inferior vertebra when implanted.

The cavity 38 of the body 11 of the TLIF implant 10 is defined by interior walls. Particularly, the cavity 38 has a first interior lateral wall (not seen) on the other side of the first lateral side 14, a second interior lateral wall 31 on the other side of the second lateral wall (not seen), a first interior end wall 33 on the other side of the first end 12, and a second interior end wall 34 on the other side of the second end 13. As best seen in FIG. 1, the second interior lateral wall 31 has an upper ledge 29 that curves upwardly from the second interior end wall 34 to approximately the first interior end wall 33. While not seen, the second interior lateral wall 31 has a lower ledge that curves downwardly from the second interior end wall 34 to approximately the first interior end wall 33. In like manner, the first interior lateral wall (not seen) has an upper ledge (not seen) that curves upwardly from the second interior end wall 34 go approximately the first interior end wall 33, and a lower ledge (not seen) that curves downwardly from the second interior wall 34 to approximately the first interior wall 33. The upper ledges 29, not seen, define an upper guide or track for an upper (superior) blade 109 (see FIG. 2) while the lower ledges not seen, not seen, define a lower guide or track for a lower (inferior) blade 108 (see FIG. 2).

Figure 2:
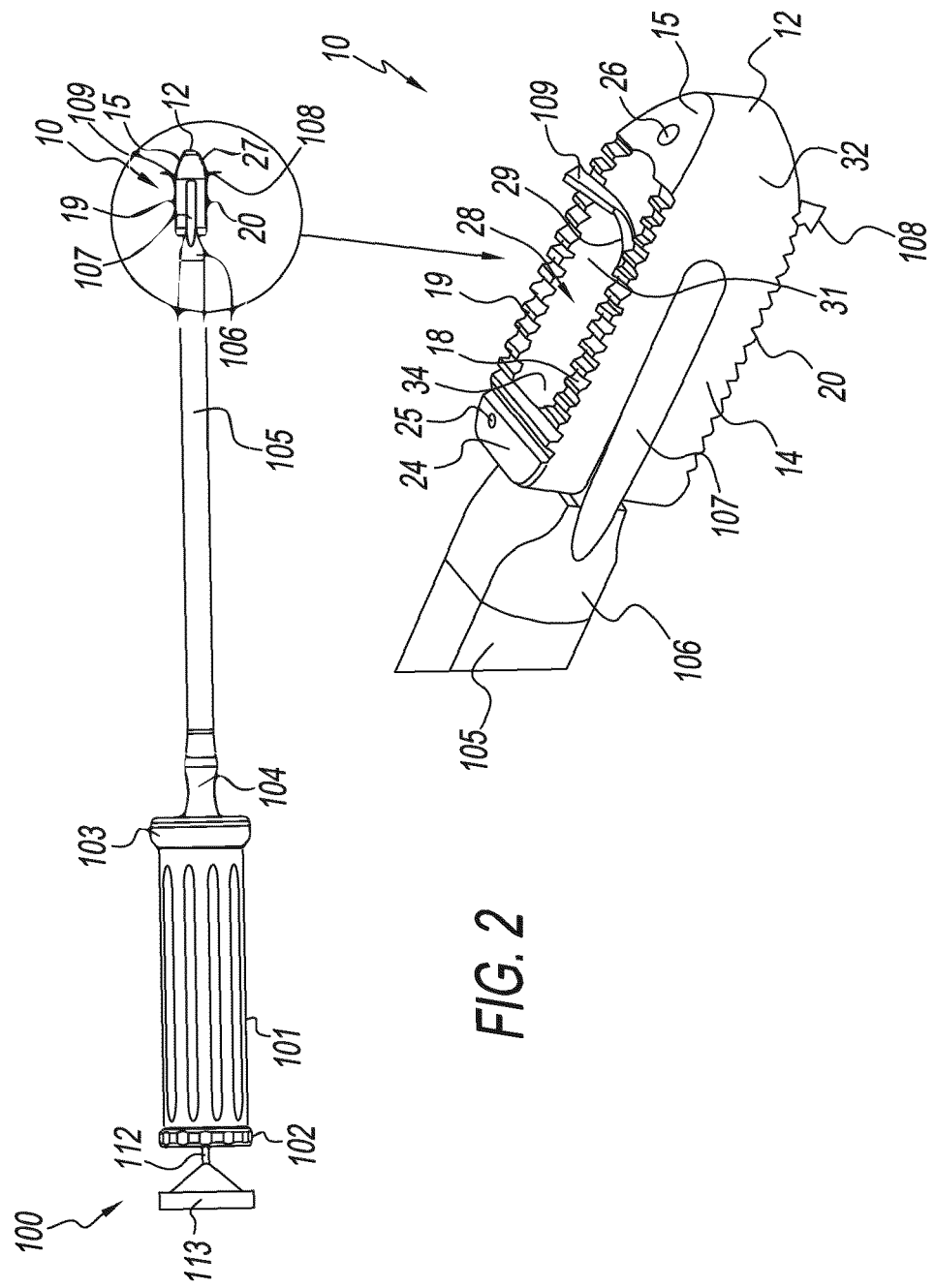
FIG. 2 is a side view of a system for installing a TLIF implant, the system showing an instrument for installing the TLIF implant of FIG. 1 with the TLIF implant situated on an insertion end of the installation instrument, the TLIF implant shown in greater detail within an enlargement insert and depicting blades of the TLIF implant in an extended position.

The upper and lower blades 109, 108 are impacted or preferably, but not necessarily, completely held within the cavity 28 of the body 11. The upper and lower blades 109, 108, however, are moveable such that distal ends of the blades extend out of the cavity 28 and beyond the body 11, such as shown in FIG. 2. When the proximate end (not seen as it is within the cavity 28) of the upper blade 109 is pushed by a pushing rod of an installation instrument/tool 100 (see below), the upper blade 109 moves along the upper tracks of the inner wall of the cavity such that the distal end of the upper blade 109 extends out of the cavity 28 and beyond the body 11. The distal end of the upper blade 109 may be pointed, barbed or otherwise sharp in order to be received in an upper (superior) spine disc and/or vertebra. When the proximate end (not seen as it is within the cavity 28) of the lower blade 108 is pushed by a pushing rod of an installation instrument/tool 100 (see below), the lower blade 108 moves along the lower tracks of the inner wall of the cavity such that the distal end of the lower blade 108 extends out of the cavity 28 and beyond the body 11. The distal end of the lower blade 108 may be pointed, barbed or otherwise sharp in order to be received in an upper (superior) spine disc and/or vertebra.

Figure 3:
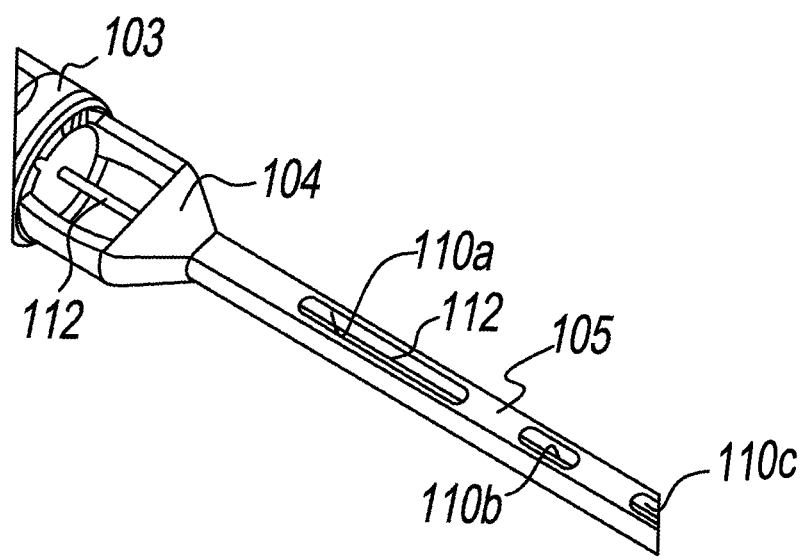
FIG. 3 is an enlarged partial view of a portion of the TLIF implant installation instrument of FIG. 2.

FIGS. 2 and 3 show an instrument or tool 100 for installing/implanting the TLIF implant 10. The instrument 100 includes a handle 101 of a generally cylindrical shape (however, other shapes may be used) with a rear end 102 and a front end 103. The rear end 102 is generally disk-shaped in like manner as the handle 101 and includes knurling on its outer surface, but other shapes may be used. The front end 103 is likewise generally disk-shaped in like manner as the handle 101, but other shapes may be used. A yoke 104 extends from the front end 103 of the handle 101 and supports a hollow shaft or cannula 105. A tip 106 is provided at the distal end of the hollow shaft 105 and provides an exit opening of the hollow shaft 105. The tip 106 has a first elongated prong 107 and a second elongated prong (not seen) opposite the first elongated prong 107, the nomenclature first and second being arbitrary. The first elongated prong 107 is configured for reception in the first elongated groove 22 of the TLIF implant 10, while the second elongated prong (not seen) is configured for reception in the second elongated groove 30 of the TLIF implant 10 in like manner to the first.

The tool 100 allows the use of a rod 112 for contacting and pushing the upper and lower blades 109, 108 out of the cavity 38 of the TLIF implant 10 after insertion. The tool 100 also allows the use of the rod 112 or other rod for inserting bone graft/bone graft material into the cavity 38 of the TLIF implant 10 after the TLIF implant 10 has been implanted and the impacted first and second blades 29 are extended. In order to accommodate the rod 112, the first and second ends 102, 103 of the handle 101 both have a central hole. The rod 112 extends through the handle 101 and the holes of the first and second ends 102, 103. The rod 112 also extends through the yoke and the hollow shaft 105. The length of the rod 112 is sufficient to extend beyond the tip 106 of the hollow shaft 105 and reach into the TLIF implant 10 when the TLIF implant 10 is held by the instrument 100, particularly the first and second elongated prongs 107, not seen, during installation of the TLIF implant 10. A knob 113 is provided at the proximal end of the rod 112 for controlling movement of the rod 112. The rod 112 may be removed from the shaft 105 and handle 101 and another rod 112 inserted in its place.

As seen in FIG. 3, the hollow shaft 105 includes one or more windows or openings, three windows 110a, 110b, and 110c of which are shown as an example. The hollow shaft 105 may have more or less than three windows as desired. The windows 110a, 110b, and 110c are generally oval in shape and are preferably, but not necessarily, all situated in the same side of the hollow shaft 105. Other shapes and positions may be used. While not necessary, the window 110a is larger than the windows 110b, 110c to allow for graft insertion and pushing into the cavity 28 of the TLIF implant 10 via the unthreaded hole 23 of the body 11. The end of one the graft insertion/pushing rods may be funnel shaped to drive the graft along the hollow shaft 105 and into the cavity 38 of the implant body 11 via the implant hole 23.

Per the method of installation, the upper and lower blades 109, 108 of the TLIF implant 10 are held or impacted within the cavity 38 of the body 11 of the TLIF implant 10 before the implant is installed (e.g. FIG. 1). While the first and second elongated prongs 107, (not seen) hold the TLIF implant 10 through reception of the first elongated prong 107 into the first elongated lateral side slot 22 of the TLIF body 11, and the second elongated prong (not seen) in the second elongated lateral side slot 30 of the TLIF body 11, the rod 112 is manipulated via the knob 113 to push the distal end of the rod (not seen) through the hole 23 and into the cavity 38 of the body 11. The distal tip (not seen) of the rod 112 is configured to push the upper blade 109 along the upper ledges 29, (not seen) of the first and second interior lateral walls 31, (not seen) of the cavity 38, and the lower blade 108 along the lower ledges (not seen) of the first and second interior lateral walls 31, (not seen) of the cavity 38. The upper blade 109 is guided along the upper ledges to project or extend the end of the upper blade 109 out of the cavity 38, as seen in FIG. 2. The lower blade 108 is guided along the lower ledges to project or extend the end of the lower blade 108 of the cavity 38, as seen in FIG. 2. The upper and lower blades 109, 108 remain extended after installation of the TLIF implant 10 to help hold the implant in place.

A method of installation includes placing an impacted blade TLIF implant 10 onto the installation instrument or tool 100. Particularly, the first and second prongs at the tip of the shaft of the installation tool are received in the first and second outside lateral slots of the impacted blade TLIF implant body. The installation tool is ready to place the implant into the vertebral space previously occupied by a vertebra, the vertebra having been surgically removed prior to implant installation. Once the impacted blade TLIF implant has been placed at the desired location, a rod 112 with a tip configured to push the impacted blades up and out of the implant cavity is used in the installation tool and is moved to expel the blades. The blade pushing rod is removed and a graft pushing rod is received in the installation tool. Graft is inserted through the windows of the tool shaft. The graft pushing rod is moved to push the graft through the shaft and into the cavity of the installed TLIF implant through the end hole. Once a sufficient amount of graft has been pushed into the implant cavity, the rod and installation tool are removed.

It should be appreciated that dimensions of the components, structures, and/or features of the present TLIF implant and installation instrument may be altered as desired within the scope of the present disclosure.

What is claimed is:

1. A kit for installing a spine implant, the kit comprising:
an installation tool; and
a spine implant;
the spine implant comprising:
a body defining a superior surface, an inferior surface, a first end of the body, a second end of the body, a first lateral side between the first end and the second end, and a second lateral side between the first end and the second end, the body having:
a cavity extending through the body from the superior surface to the inferior surface;
a channel extending a first length along the first lateral side; a bore extending through the second end of the body and in communication with the cavity;
a first superior guide and a second superior guide in the cavity defining a superior blade guide;
a first inferior guide and a second inferior guide in the cavity defining an inferior blade guide;
a first blade situated on the superior blade guide and held in the cavity during implantation of the body but movable along the superior blade guide after implantation of the body such that a distal end of the first blade extends out of the cavity from the superior surface and beyond the body; and a second blade situated on the inferior blade guide and held in the cavity during implantation of the body but movable along the inferior blade guide after implantation of the body such that a distal end of the second blade extends out of the cavity from the inferior surface and beyond the body; and the installation tool comprising:

a handle;

a hollow shaft connected to the handle and having a tip with a first prong configured to be received in the channel on at least the first lateral side of the body of the implant during installation thereof;

a pusher rod configured to extend through the hollow shaft and extend the first and second blades; and a graft rod configured to extend through the hollow shaft and introduce graft material into the spine implant.

2. The kit of claim 1, further comprising:

first serrations on the superior surface of the body of the implant; and second serrations on the inferior surface of the body of the implant.

3. The kit of claim 1, wherein the distal end of the first blade of the implant has a first barb; and the distal end of the second blade of the implant has a second barb.

4. The kit of claim 1, wherein the channel of the implant extends a second length along a second lateral side of the body, the second lateral side of the body arranged opposite the body from the first lateral side.

5. The kit of claim 4, wherein the channel of the implant extends from the bore in the second end along the first length of the first lateral side of the body and along the second length of the second lateral side of the body.

6. The kit of claim 4, wherein the first length and the second length extend to proximate the first end of the body of the spine implant.

7. The kit of claim 1, wherein the hollow shaft of the installation tool has one or more openings configured to allow graft material to be inserted into the hollow shaft of the installation tool.

8. The kit of claim 1, wherein the hollow shaft of the installation tool has a plurality of openings configured to allow graft material to be inserted into the hollow shaft of the installation tool.

* * * * *